(12) United States Patent  
Sparks et al.

(10) Patent No.: US 7,228,735 B2
(45) Date of Patent: Jun. 12, 2007

(54) FLUID SENSING DEVICE WITH INTEGRATED BYPASS AND PROCESS THEREFOR

(75) Inventors: Douglas Ray Sparks, Whitmore Lake, MI (US); Nader Najafi, Ann Arbor, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 22 days.

(21) Appl. No.: 11/164,374

(22) Filed: Nov. 21, 2005

(65) Prior Publication Data

US 2006/0169038 A1 Aug. 3, 2006

Related U.S. Application Data

(60) Provisional application No. 60/649,105, filed on Feb. 3, 2005, provisional application No. 60/656,814, filed on Feb. 28, 2005.

(51) Int. Cl.
*G01F 1/68* (2006.01)
(52) U.S. Cl. .................................................. 73/204.26
(58) Field of Classification Search ............. 73/204.26, 73/862.352, 204.25, 204.23, 861.355, 861.04
See application file for complete search history.

(56) References Cited

U.S. PATENT DOCUMENTS

| | | | | |
|---|---|---|---|---|
| 4,729,243 A | * | 3/1988 | Friedland et al. | 73/861.355 |
| 5,361,035 A | | 11/1994 | Meitzler et al. | 324/663 |
| 5,717,136 A | * | 2/1998 | Aoi et al. | 73/204.26 |
| 5,861,561 A | | 1/1999 | Van Cleve et al. | |
| 5,969,264 A | * | 10/1999 | Rivkin | 73/861.356 |
| 6,164,140 A | * | 12/2000 | Kalinoski | 73/861.357 |
| 6,477,901 B1 | | 11/2002 | Tadigadapa et al. | 73/861.352 |
| 6,488,837 B1 | | 12/2002 | Ren et al. | 205/787 |
| 6,647,778 B2 | | 11/2003 | Sparks | 73/204.26 |
| 6,696,189 B2 | | 2/2004 | Bostaph et al. | 429/22 |
| 6,803,775 B2 | | 10/2004 | Sanchez et al. | 324/698 |
| 6,842,017 B2 | | 1/2005 | MeKenzie et al. | 324/663 |
| 2004/0255648 A1 | | 12/2004 | Sparks | |

FOREIGN PATENT DOCUMENTS

GB 2221302 1/1990

OTHER PUBLICATIONS

Motoralla Presentation; 2002 Fuel Cell Seminar; Nov. 18-21, 2002; J. Bostaph.
"CeBIT 2003—Portable Fuel Cells," Fuel Cells Today; Mar. 19, 2003; S. Geiger.

(Continued)

*Primary Examiner*—Jewel Thompson
(74) *Attorney, Agent, or Firm*—Gary M. Hartman; Domenica N. S. Hartman; Hartman & Hartman

(57) ABSTRACT

A micromachined fluid sensing device and a method for its fabrication. The sensing device incorporates a bypass passage, preferably an integral bypass passage within the device, that enables a volume of fluid to be delivered to the device, with a limited portion of the fluid passing through a passage within the device in which one or more properties of the fluid are sensed, such as but not limited to density, specific gravity, and chemical concentrations. The device is suitable for monitoring the fuel concentration in a fuel mixture for a fuel cell.

18 Claims, 3 Drawing Sheets

OTHER PUBLICATIONS

"Micro Fuel Cells Headed to Market and a Showdown," Small Times; Mary 27, 2004; J. Mason.

"MTI Micro Fuel Cells . . . ," EE Times, p. 30; Jan. 2003; J. Walko.

"Company unveils laptop computer that runs on methanol," AP; Jun. 30, 2003.

"Reducing methanol corsssover in CH3OH fuel cell membranes," NASAtech briefs; S. Fedor.

"Methanol sensors for use in fuel cell pwer sources," Electrochem. & Solid State Letters, vol. 3., 117; 2000.

"Portable direct methanol fuel cell systems components and integration," 2003 Fuel Cell Seminar; Nov. 2003; C. Martin and J. Martin.

"A variable temperatures, resonant density sensor made using an improved chip-level vacuum package," Sensors and Actuators A, vol. 107, pp. 119-124; 2003; D. Sparks, R. Smith, R. Schneider, J. Cripe, S. Massoud-Ansari, A. Chimbayo, N. Najafi.

"A Microfulidic System for the measurement of Chemical Concentration and Density," Transducers 2003, Boston, MA, 2C2.5, p. 300-303; Jun. 2003; D. Sparks, R. Smith, M. Straayer, J. Cripe, R. Schneider, S. Ansari, N. Najafi.

"In-Line Chemical Concentration Sensor," Proceedings Sensors Expo Spring 2003, Chicago, IL; Jun. 2003; D. Sparks, R. Schneider, R. Smith, A. Chimbayo, J. Cripe, M. Straayer, N. Najafi.

"Measurement of Density and Chemical Concentration Using a Microfluidic Chip," Lab Chip, vol. 3, p. 19-21; 2003; D. Sparks, R. Smith, M. Straayer, J. Cripe, R. Schneider, A. Chimbayo,, S. Ansari, N. Najafi.

"A silicon resonant sensor structure for Coliolis mass-flow measurement," Jor. MEMS vol. 6, p. 119; 1997; P. Enoksson, G. Stemme and E. Stemme.

* cited by examiner

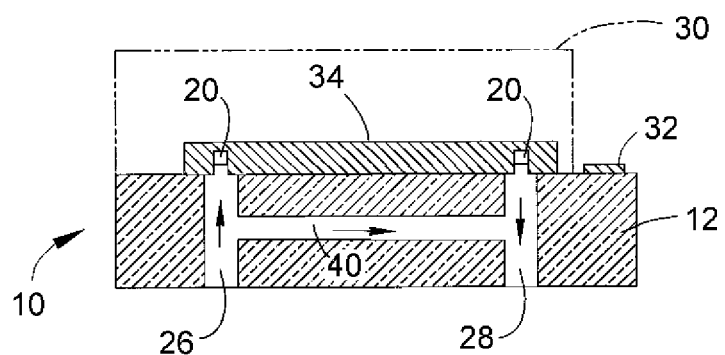
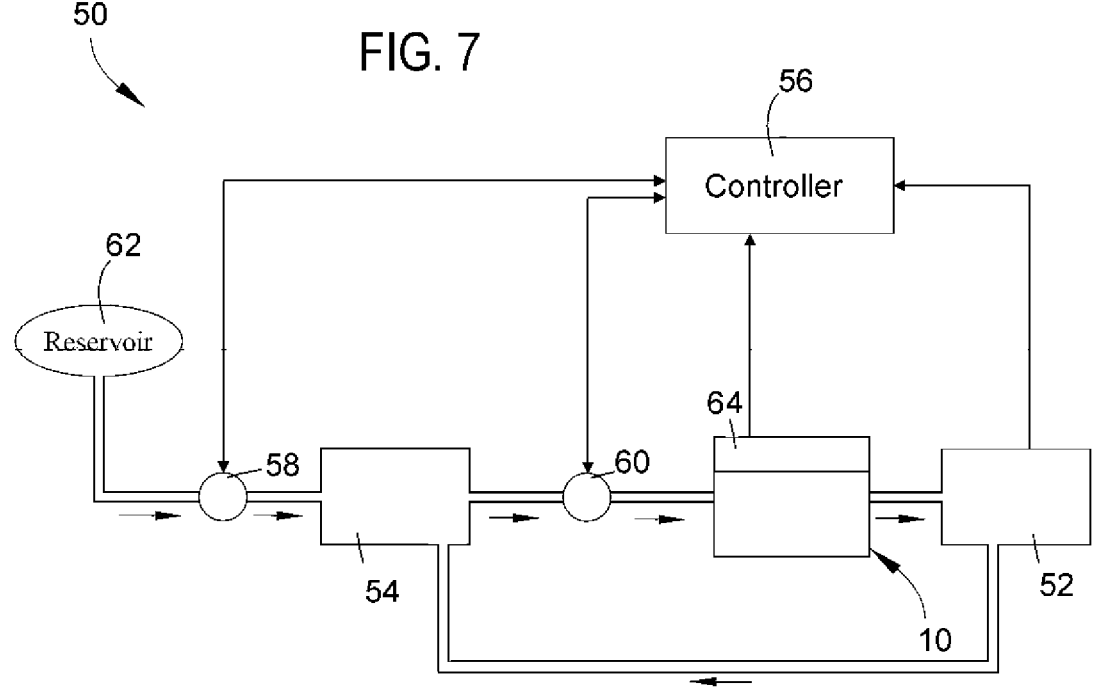

FLUID SENSING DEVICE WITH INTEGRATED BYPASS AND PROCESS THEREFOR

CROSS REFERENCE TO RELATED APPLICATIONS

This application claims the benefit of U.S. Provisional Application No. 60/649,105, filed Feb. 3, 2005, and U.S. Provisional Application No. 60/656,814, filed Feb. 28, 2005, the contents of both being incorporated herein by reference.

BACKGROUND OF THE INVENTION

The present invention generally relates to fluid sensing devices and process for producing such devices. More particularly, this invention relates to a micromachined fluid sensing device capable of measuring properties such as fluid density, specific gravity, and chemical concentrations, and in which a fluid bypass is integrated into the device to enable use of the device in flow systems that exceed the internal flow capacity of the device.

Processes and designs for resonant mass flow and density sensors using silicon micromachining techniques are disclosed in commonly-assigned U.S. Pat. No. 6,477,901 to Tadigadapa et al. and U.S. Pat. No. 6,647,778 to Sparks. As used herein, micromachining is a technique for forming very small elements by bulk etching a substrate (e.g., a silicon wafer), or by surface thin-film etching, the latter of which generally involves depositing a thin film (e.g., polysilicon or metal) on a sacrificial layer (e.g., oxide layer) on a substrate surface and then selectively removing portions of the sacrificial layer to free the deposited thin film. In the processes disclosed by Tadigadapa et al. and Sparks, wafer bonding and silicon etching techniques are used to produce microelectromechanical systems (MEMS) comprising one or more suspended silicon tubes on a wafer. The tube is vibrated at resonance, by which the flow rate and density of a fluid flowing through the tube can be determined.

Sensors of the type taught by Tadigadapa et al. and Sparks have found use in a variety of applications. A notable advantage of these sensors is the extremely miniaturized scale to which they can be fabricated, which among other things enables the sensors to precisely analyze very small quantities of fluids. However, in certain applications where relatively large volume flow rates exist, the limited flow capacity of these miniaturized sensors can be inadequate. It would be advantageous if sensors of the type taught by Tadigadapa et al. and Sparks could be adapted for relatively high flow applications without necessitating an increase in sensor size.

BRIEF SUMMARY OF THE INVENTION

The present invention provides a micromachined fluid sensing device and a method for its fabrication. The sensing device incorporates a bypass passage, preferably an integral bypass passage within the device, that enables a volume of fluid to be delivered to the device, with a limited portion of the fluid passing through a passage within the device in which one or more properties of the fluid are sensed, such as but not limited to density, specific gravity, and chemical concentrations. As an example, this invention can be used to monitor the water to fuel ratio in a fuel cell, examples of such fuels including but not limited to methanol, ethanol, isopropyl alcohol (IPA), formic acid, sulfuric acid, gasoline, and other organic liquids.

According to a first aspect of the invention, the fluid sensing device of this invention comprises a micromachined tube that includes a base, a fluid inlet and a fluid outlet in the base, a freestanding portion extending from the base, and a continuous passage within the freestanding portion. The continuous passage is fluidically connected to the fluid inlet and the fluid outlet so as to accommodate a fluid flowing through the micromachined tube. The sensing device further includes a substrate having a surface to which the tube base is attached, such that the freestanding portion of the micromachined tube is suspended over the substrate so as to be spaced apart therefrom. The tube base is spaced apart from the substrate surface so as to define a gap therebetween in a direction normal to the substrate surface. The substrate has first and second passages having openings at the substrate surface, and the first and second passages are fluidically connected to the fluid inlet and fluid outlet, respectively, of the micromachined tube, whereby the first and second passages of the substrate are fluidically coupled through the continuous passage of the micromachined tube. A bypass passage is defined by and between the tube base and the substrate surface. In addition to being fluidically coupled through the continuous passage of the micromachined tube, the first and second passages of the substrate are also fluidically coupled through the bypass passage, thereby enabling a first portion of a fluid flowing from the first passage of the substrate to the second passage of the substrate to flow through the bypass passage while a second portion of the fluid flows through the continuous passage of the micromachined tube. A fluid-tight sealing material is within the gap between the tube base and the substrate surface, and surrounds the openings of the first and second passages of the substrate and the fluid inlet and outlet of the micromachined tube to define a boundary of the bypass passage in a plane parallel to the substrate surface. The sensing device further includes means for vibrating the freestanding portion of the micromachined tube at a resonant frequency thereof, and means for sensing movement of the freestanding portion of the micromachined tube.

According to a second aspect of the invention, a method is provided for fabricating a fluid sensing device comprising a micromachined tube having a base, a freestanding portion extending from the tube base, a fluid inlet and a fluid outlet in the tube base, and a continuous passage within the freestanding portion and fluidically connecting the fluid inlet to the fluid outlet. The method employs a substrate having a surface and first and second passages with openings at the substrate surface, and includes attaching the tube base to the substrate surface so that the tube base is spaced apart from the substrate surface and a gap is defined therebetween in a direction normal to the substrate surface. The step of attaching the tube base to the substrate surface results in a bypass passage being defined by and between the base and the surface. Furthermore, the tube base is attached so that the freestanding portion of the micromachined tube is suspended over the substrate and spaced apart therefrom, and the fluid inlet and the fluid outlet in the base are fluidically connected to the first and second passages, respectively, of the substrate, whereby the first and second passages of the substrate are fluidically coupled through the continuous passage of the micromachined tube. Finally, attachment of the tube base to the substrate surface is carried out so that a fluid-tight sealing material is disposed within the gap between the tube base and the substrate surface. The sealing material surrounds the openings of the first and second passages of the substrate and the fluid inlet and outlet of the micromachined tube to define a boundary of the bypass passage in a plane parallel to the substrate surface. As a result of the above process, a fluid flowing into the sensing device through the first passage of the substrate flows out of the sensing device through the second passage, and a first portion of the fluid flows through the bypass passage while a second portion of the fluid flows through, in succession, the fluid inlet in the base, the continuous passage of the micromachined tube, and the fluid outlet in the base. During fluid flow, the freestanding portion of the micromachined tube is vibrated at a resonant frequency thereof, and movement of the freestanding portion of the micromachined tube is sensed.

In view of the above, it can be seen that the present invention provides for a miniature, micromachined fluid sensing device and process for producing a fluid sensing device, in which the device itself incorporates a bypass passage. As such, excess fluid flow into the device can be internally bypassed without any bypass system extraneous to the device. Because the bypass passage can be defined by and between the base of the tube and the surface of the substrate during attachment of the base to the substrate surface, complicated processing measures are not required to define the bypass passage. Furthermore, the sealing material or an additional means can be used to establish and control the width of the gap between the substrate surface and tube base, and in doing so helps to define the depth of the bypass passage. Finally, alternative bypass configurations are possible and can be employed with the invention, including bypass passages within the bulk of the substrate and bypass passages external to the substrate.

The resulting sensing device is well suited for a variety of applications, such as sensing the density, specific gravity, or chemical concentrations of a fluid. A notable example is the sensing of fuel concentrations in fuel mixtures for fuel cell systems. The sensing device can also be configured to sense multiple other fluid properties, such as flow rate, pH, temperature, etc. The fluid flowing through the bypass passage can be evaluated to determine these additional properties.

Other objects and advantages of this invention will be better appreciated from the following detailed description.

BRIEF DESCRIPTION OF THE DRAWINGS

FIG. 6 is a cross-sectional view through the base of the tube and the substrate to which the base is attached in accordance with a third embodiment of this invention.

FIG. 7 schematically represents a fluid sensing device of this invention installed in a fuel cell system.

DETAILED DESCRIPTION OF THE INVENTION

Figure 1:
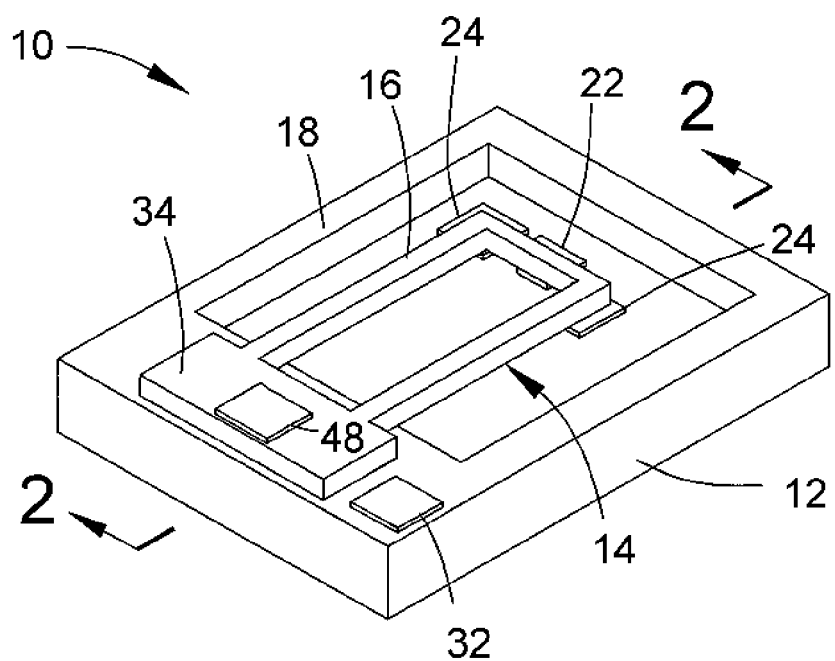
FIGS. 1 and 2 are plan and cross-sectional views, respectively, of a fluid sensing device with a micromachined tube in accordance with an embodiment of this invention.
Figure 2:
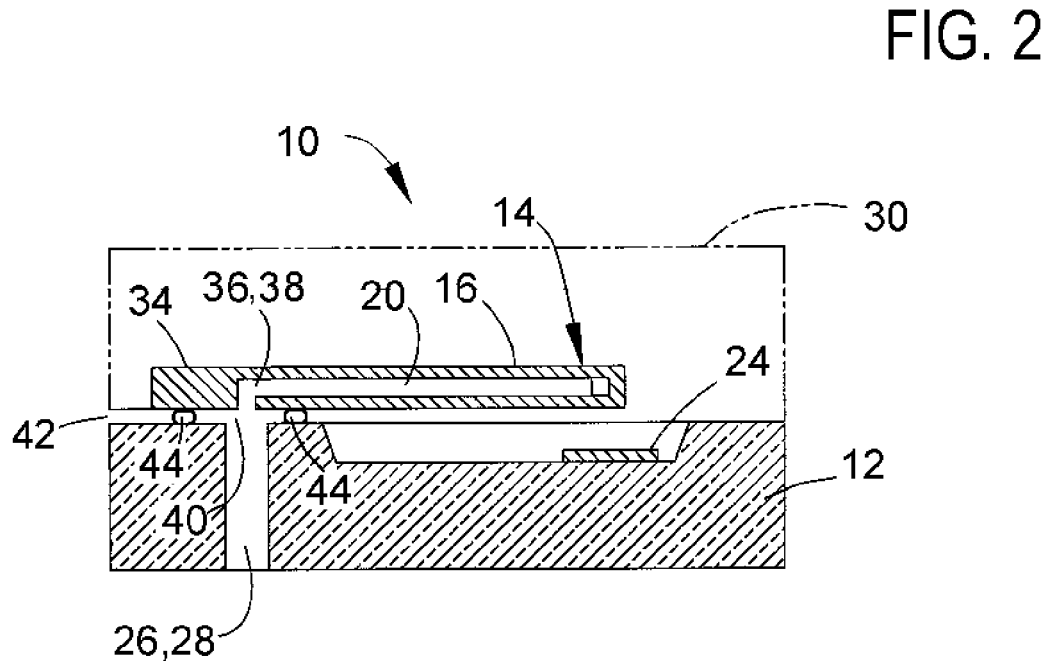

FIGS. 1 and 2 represent a sensing device 10 of a type disclosed in commonly-assigned U.S. Pat. No. 6,477,901 to Tadigadapa et al., and suitable for describing the present invention. The device 10 is represented as including a substrate 12 that may be formed of silicon or another semiconductor material, quartz, glass, ceramic, metal, a polymeric material, a composite material, etc. A tube 14 is supported by the substrate 12 so as to have a base 34 attached to a surface 18 of the substrate 12, a fluid inlet 36 and fluid outlet 38 within the base 34, and a freestanding portion 16 suspended above the substrate 12. A continuous passage 20 is present within the tube 14 and fluidically couples the inlet 36 to the outlet 38 of the tube 14. According to a preferred aspect of the invention, the tube 14 is micromachined from silicon or another semiconductor material, quartz, ceramic, metal, or composite material. The substrate 12 and tube 14 are fabricated separately, after which the tube 14 is attached as a unitary member to the surface 18 of the substrate 12, as will be discussed in more detail below.

The tube 14 is shown in FIGS. 1 and 2 as being adapted to serve as a conduit through which a fluid flows while the tube 14 is vibrated for the purpose of ascertaining certain properties of the fluid, preferably using Coriolis force principles in accordance with the aforementioned Tadigadapa et al. patent, whose contents relating to the fabrication and operation of a Coriolis-based sensor are incorporated herein by reference. The freestanding portion 16 of the tube 14 is generally U-shaped, though other shapes—both simpler and more complex—are within the scope of this invention. The freestanding portion 16 is vibrated in a direction perpendicular to the surface 18 of the substrate 12, preferably at or near its resonant frequency. Fluid enters the device 10 through a fluid inlet passage 26 in the substrate 12 and exits the device 10 through a fluid outlet passage 28, both of which are represented in FIG. 2 as being etched or otherwise formed to extend through the substrate 12. During half of the vibration cycle in which the tube 14 moves upward, the freestanding portion 16 has upward momentum as the fluid travels around the tube bends, and the fluid flowing out of the freestanding portion 16 resists having its vertical motion decreased by pushing up on that part of the freestanding portion 16 nearest the fluid outlet 38. The resulting force causes the freestanding portion 16 of the tube 14 to twist. As the tube 14 moves downward during the second half of its vibration cycle, the freestanding portion 16 twists in the opposite direction. This twisting characteristic is referred to as the Coriolis effect, and the degree to which the freestanding portion 16 of the tube 14 deflects during a vibration cycle as a result of the Coriolis effect can be correlated to the mass flow rate of the fluid flowing through the tube 14, while the density of the fluid is proportional to the frequency of vibration.

The tube 14 is preferably driven at resonance, with the resonant frequency of the tube 14 being controlled by its mechanical design (shape, size, construction and materials). Resonant frequencies will generally be in the range of about 1 kHz to about 100 kHz. The amplitude of vibration is preferably adjusted through the means used to vibrate the tube 14. As shown in FIGS. 1 and 2, a drive electrode 22 is located beneath the tube 14 on the substrate 12. In this embodiment, the tube 14 is formed of doped silicon and can therefore serve as an electrode that can be capacitively coupled to the drive electrode 22, enabling the electrode 22 to capacitively (electrostatically) drive the tube 14. However, it is foreseeable that the tube 14 could be formed of a nonconductive material, and a separate electrode formed on the tube 14 opposite the electrode 22 for vibrating the tube 14 electrostatically. An alternative driving technique is to provide a piezoelectric element on an upper surface of the tube 14 to generate alternating forces in the plane of the tube 14 that flex the freestanding portion 16 of the tube 14 in directions normal to the plane of the tube 14. Other alternatives are to drive the freestanding portion 16 of the tube 14 magnetically, thermally, or by another actuation technique. Also shown in FIGS. 1 and 2 are sensing electrodes 24 for providing feedback to the drive electrode 22 to enable the vibration frequency to be controlled with appropriate circuitry (not shown) while also sensing the deflection of the tube 14 relative to the substrate 12. The sensing electrodes 24 can sense the tube 14 capacitively or in any other suitable manner capable of sensing the proximity or motion of the tube 14.

In FIG. 2, the sensing device 10 is schematically shown as enclosed by a cap 30 to form a sensing package. The cap 30 allows for vacuum packaging that reduces air damping of the tube vibration. A variety of package and wafer-level methods exist and are well known for vacuum packaging electronic devices, and therefore will not be discussed here in any detail. Such methods include solder or weld hermetic packages, and wafer bonding using glass frit, solder, eutectic alloy, adhesive, and anodic bonding. A suitable material for the cap 30 is silicon, though it is foreseeable that a variety of other materials could be used including metals and glass materials, the latter including borosilicate glass (e.g., Pyrex). Input and output signals to the device 10 are made through bond pads 32 (only one of which is shown) outside the cap 30. In the preferred embodiment of this invention, the bond between the cap 30 and the substrate 12 is hermetic, and the enclosure formed by the substrate 12 and cap 30 is evacuated to enable the tube 14 to be driven efficiently at high quality (Q) values without damping. In such an embodiment, a getter material is preferably placed in the enclosure to assist in reducing and maintaining a low cavity pressure. As an alternative to a hermetically sealed package, the tube 14 could be enclosed such that a vacuum can be drawn when desired through the use of a pump.

The device 10 is also shown in FIG. 2 as including a sensing element 48 for measuring the temperature of the fluid flowing through the tube 14. Properties such as densities of materials change with temperature, as do the Young's and shear moduli of materials. Placement of the temperature sensing element 48 on the base 34 of the tube 14 enables the temperature of the tube 14 and its fluid contents to be monitored with suitable accuracy under many operating conditions. A suitable construction for the sensing element 48 can make use of one or more metal layers of the type employed to form the electrodes 22, 24, and 32, and their associated conductive runners. For example, a resistive-based temperature sensing element 48 can be formed by a thin-film metal layer of platinum, palladium or nickel, in accordance with known practices. With the temperature sensing element 48, changes in mechanical properties of the tube 14 and properties of the fluid therein attributable to temperature changes can be compensated for with appropriate circuitry (not shown). Alternatively or in addition, an electrical potential could be applied to pass a current through the tube 14 to raise and maintain the temperature of the tube 14 and the fluid flowing therethrough by Joule heating, with the sensing element 48 used as feedback for appropriate control circuitry (not shown).

The shape and size of the tube 14 are chosen to provide a suitable flow capacity and have suitable vibration parameters for the fluid to be evaluated with the device 10. Because micromachining technologies are employed to fabricate the tube 14, the size of the tube 14 can be extremely small, such as lengths of about 0.5 mm and cross-sectional areas of about 250 square micrometers, with smaller and larger tubes also being within the scope of this invention.

Because of the ability to produce the tube 14 at such miniaturized sizes, the device 10 can be used to process very small quantities of fluid for analysis. However, because miniaturization can render the device 10 unsuited for applications in which measurements of properties are desired for a fluid flowing at relatively high flow rates, the device 10 is shown in FIG. 2 as being configured to have an internal bypass passage 40 having a cross-sectional flow area that is relatively larger than the cross-sectional flow area of the passage 20 within the tube 14. As evident from FIGS. 2 and 3 (the latter corresponding to a cross-section of the device 10 transverse to the cross-section of FIG. 2), the bypass passage 40 is fluidically in parallel with the passage 20 through the tube 14, and therefore allows excess fluid entering the device 10 through the inlet passage 26 to be routed directly to the outlet passage 28 instead of to the tube 14.

Figure 3:
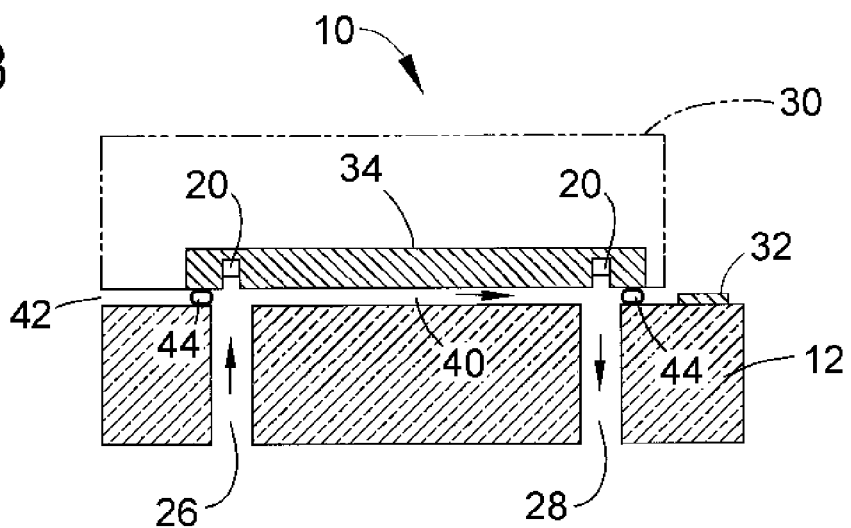
FIG. 3 is a cross-sectional view through the base of the tube and the substrate to which the base is attached in accordance with a first embodiment of this invention.

In FIGS. 2 and 3, the bypass passage 40 is defined entirely by a gap 42 between the substrate surface 18 and the base 34 of the tube 14. In turn, the gap 42 is represented in FIGS. 2 and 3 as coinciding with and preferably determined by the height of a seal 44 between the base 34 and substrate surface 18. The seal 44 is preferably continuous and surrounds the openings of both passages 26 and 28 at the surface 18 of the substrate 12, and therefore also the inlet and outlet 36 and 38 to which the passages 26 and 28, respectively, are fluidically coupled. Suitable materials for the seal 44 include adhesives and solders that can be deposited on the substrate surface 18 or tube base 34, and discreet components such as O-rings, gaskets, washers, and compressed seals that can be individually placed and secured between the surface 18 and base 34. If an adhesive or solder, the seal 44 can be used to bond the base 34 to the substrate 12.

To provide a suitable bypass functionality, the bypass passage 40 preferably has a cross-sectional area greater than that of the passage 20 within the tube 12. While suitable control of the cross-sectional area of the passage 40 can be achieved for many applications solely by choosing an appropriate type of seal 44, a seal 44 formed by an adhesive or solder can benefit from beads or other particles of controlled and uniform size. By pressing the tube base 34 onto the substrate surface 18 until individual beads within the seal 44 are trapped between and contact both the base 34 and surface 18, the gap 42 (and therefore the height of the bypass passage 40) can be established by the diameter of the beads. Because the seal 44 defines the outermost boundaries of the bypass passage 40 in the plane of the substrate surface 18, the cross-sectional area of the passage 40 can be readily controlled through placement of the seal 44 relative to the openings of the passages 26 and 28 at the substrate surface 18.

Figure 4:
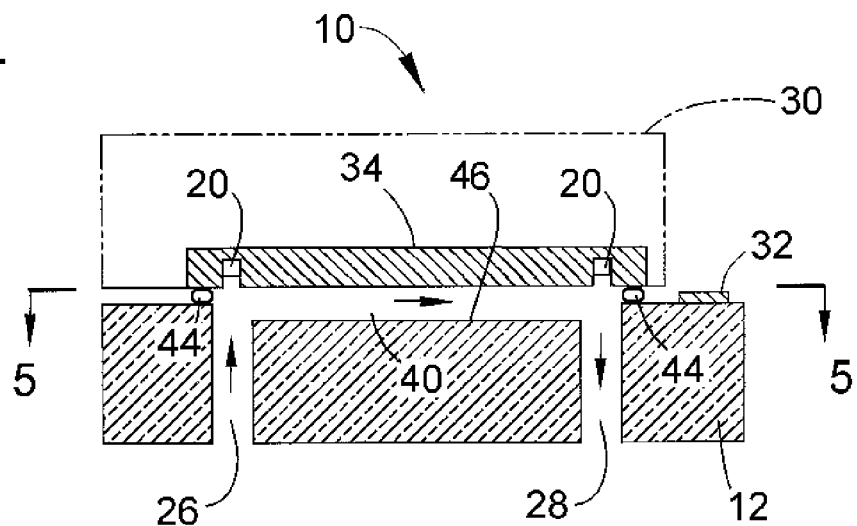
FIG. 4 is a cross-sectional view through the base of the tube and the substrate to which the base is attached in accordance with a second embodiment of this invention.
Figure 5:
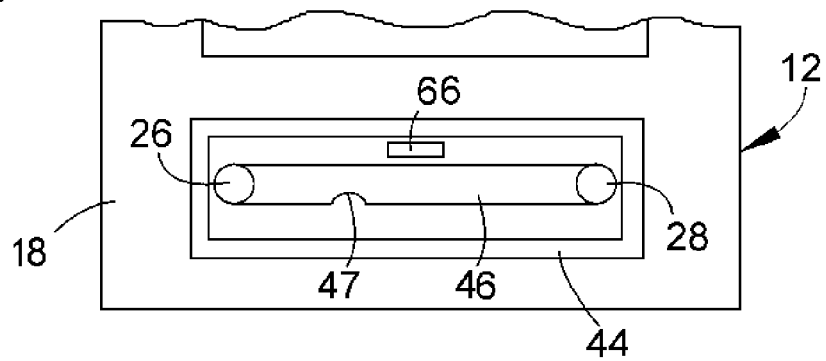
FIG. 5 is a partial plan view of the substrate of FIG. 4.

The cross-sectional area of the bypass passage 40 can be further increased by forming a recess in the substrate surface 18 between the passages 26 and 28 and/or the base 34 between the inlet 36 and outlet 38. FIGS. 4 and 5 illustrate such an embodiment, in which elements similar to elements of FIGS. 1 through 3 are identified with the same corresponding reference numbers. In FIGS. 4 and 5, a single recess 46 has been formed in the surface 18 of the substrate 12, with the recess 46 being continuous and interconnecting the openings to the passages 26 and 28 at the substrate surface 18. Depending on the material of the substrate 12, the recess 46 can be machined, molded, stamped, etched, or otherwise formed in the substrate surface 18. As evident from FIG. 4, the depth of the bypass passage 40 in the direction normal to the substrate surface 18 equals the sum of the width of the gap 42 and the depth of the recess 46 in the direction normal to the substrate surface 18. From FIG.

5, it can be seen that the seal 44 defines the outermost boundaries of the bypass passage 40 in the plane of the substrate surface 18. As such, the depth (in the direction normal to the substrate surface 18) and width (in the plane of the substrate surface 18) of the recess 46 can be selected to obtain a desired ratio for the amount of fluid that will flow through the tube 14 relative to the amount of fluid that will flow through the bypass passage 40 without changing the configuration or processing of the tube 14. To ensure that adequate flow occurs through the passage 20 of the tube 14, the recess 46 is shown in FIG. 5 as having a protrusion 47 that acts as a flow restrictor, thereby raising the pressure within the bypass passage 40. In additional or alternatively, the seal 44 could be configured to have a portion that protrudes toward the recess 46 to provide a similar function.

Finally, FIG. 6 represents an embodiment of the invention in which the internal bypass passage 40 of the device 10 is entirely within the bulk of the substrate 12. As with the previous embodiments, the bypass passage 40 is fluidically in parallel with the passage 20 through the tube 14, and therefore allows excess fluid entering the device 10 through the inlet passage 26 to be routed directly to the outlet passage 28 instead of to the tube 14. As with the previous configurations of this invention, placement of the bypass passage 40 within the device 10 is more compact than would be if a bypass were outside the device 10, such as a bypass tube interconnecting tubes carrying the fluid to and from the inlet and outlet passages 26 and 28 of the substrate 12.

The substrate 12 can generally be fabricated from a metal, glass, or plastic material and its features formed by machining, stamping, etc., though it is also foreseeable that the substrate 12 could be formed of a semiconductor material and its features formed by bulk etching or surface thin-film etching processes known in the art. Surface thin-film techniques can also be used to form the tube 14. An example is to form the tube 14 of layers deposited on a silicon wafer, bonding the wafer to the substrate 12 so that the base 34 of the tube 14 is bonded to the surface 18 of the substrate 12 and the freestanding portion 16 is suspended over a cavity etched in the surface 18 of the substrate 12, and then removing the wafer by selective etching. These and other potential micromachining techniques are well known in the art and within the scope of this invention.

The devices 10 represented in FIGS. 1 through 6 can be used to evaluate a variety of fluids, including gases and liquids such as lubricating oils, fuels, industrial chemicals, biological fluids such as urine and blood, beverages, pharmaceutical mixtures, water, etc. Furthermore, a variety of fluid properties can be measured with the devices 10, including but not limited to density (including properties that can be correlated to density, such as specific gravity and chemical concentration), flow rate (including mass and volumetric flow rates), chemical concentrations, pH, dose, dose rate, etc. Applications in which the devices 10 can be used include fluid testing and monitoring, drug infusion and discovery, gas testing, dialysis, blood and drug monitoring, urology, etc. As such, and due to their potentially very small size, the devices 10 can find use in a variety of technical applications, including industrial applications, computer/electronic power, automotive, aerospace, fuel cell, and medical systems. As a particular example, a fuel cell system 50 is schematically represented in FIG. 7 as containing a fluid sensing device 10 of this invention. Uses for fuel cell systems are being developed for computers, lap top computers, cellular telephones, digital cameras, video cameras, motorized vehicles, motorized bicycles, recharging stations, televisions, and radios, among others. The device 10 is installed for sensing the concentration of a fuel, such as methanol, ethanol, isopropyl alcohol (IPA), formic acid, sulfuric acid, gasoline, or other organic liquid, in a mixture delivered to a fuel cell 52, such as a direct methanol fuel cell (DMFC), proton exchange membrane (PEM) fuel cell (or PEMFC), or reformed fuel cell. As well known in the art, in a fuel cell system it is important to know the concentration of the fuel in the fuel mixture to optimize the efficiency of the system. If a methanol-water mixture is used in the fuel cell 52 of FIG. 7, fluid density of the mixture can be used to determine the concentration of methanol in the mixture, thereby providing feedback for the purpose of controlling the mixing ratio or flow rate of the fuel mixture.

The device 10 of this invention is shown mounted to a line carrying a fuel-water mixture from a mixing chamber 54 to the fuel cell 52. With reference to FIGS. 2 through 4 and 6, the line carrying the mixture to the device 10 would be connected to the inlet passage 26 and the line carrying the mixture from the device 10 to the fuel cell 52 would be connected to the outlet passage 28. Control circuitry 64 noted above as useful or required by the invention is represented as being fabricated on a chip that can be mounted or otherwise appropriately coupled to the device 10 in any known manner. A system controller 56 is represented as receiving output from the device 10 and fuel cell 52, and as controlling pumps 58 and 60 that deliver the fuel from a reservoir 62 to the mixing chamber 54 and from the mixing chamber 54 to the fluid sensing device 10, respectively. The components illustrated in FIG. 7 are for illustration only, and those skilled in the art will appreciate that the fluid sensing devices 10 of this invention can be used in combination with a variety of other components and sensors, including hotwire technology to measure the mixture flow rate in the fuel cell system 50. Notably, such an additional sensor can be placed directly in the bypass passage 40 of this invention, as represented by a sensor element 66 in the bypass passage 40 of FIG. 5.

While the invention has been described in terms of certain embodiments, it is apparent that other forms could be adopted by one skilled in the art. Therefore, the scope of the invention is to be limited only by the following claims.

What is claimed is:

1. A fluid sensing device comprising:

a micromachined tube comprising a base, a fluid inlet and a fluid outlet in the base, a freestanding portion extending from the base, and a continuous passage within the freestanding portion, the continuous passage being fluidically connected to the fluid inlet and the fluid outlet so as to accommodate a fluid flowing through the micromachined tube;

means for vibrating the freestanding portion of the micromachined tube at a resonant frequency thereof;

means for sensing movement of the freestanding portion of the micromachined tube;

a substrate having a surface to which the base of the micromachined tube is attached, the base of the micromachined tube being spaced apart from the surface of the substrate so as to define a gap therebetween in a direction normal to the surface of the substrate, the freestanding portion of the micromachined tube being suspended over the substrate so as to be spaced apart therefrom, the substrate having first and second passages having openings at the surface of the substrate, the first and second passages being fluidically connected to the fluid inlet and fluid outlet, respectively, of the micromachined tube, whereby the first and second passages of the substrate are fluidically coupled through the continuous passage of the micromachined tube;

a bypass passage defined by and between the base of the micromachined tube and the surface of the substrate, the first and second passages of the substrate being fluidically coupled through the bypass passage and thereby enabling a first portion of a fluid flowing from the first passage of the substrate to the second passage of the substrate to flow through the bypass passage while a second portion of the fluid flows through the continuous passage of the micromachined tube; and a fluid-tight sealing material within the gap between the base of the micromachined tube and the surface of the substrate, the sealing material surrounding the openings of the first and second passages of the substrate and the fluid inlet and outlet of the micromachined tube and defining a boundary of the bypass passage in a plane parallel to the surface of the substrate.

2. The sensing device according to claim 1, wherein the bypass passage and the gap have equal maximum dimensions in a direction normal to the surface of the substrate that are determined entirely by the sealing material.

3. The sensing device according to claim 1, further comprising a recess in at least one of the base of the micromachined tube and the surface of the substrate, the gap and the recess having maximum dimensions in a direction normal to the surface of the substrate, the bypass passage having a maximum dimension in a direction normal to the surface of the substrate that is the sum of the maximum dimensions of the gap and the recess.

4. The sensing device according to claim 3, wherein the recess is exclusively defined in the surface of the substrate and extends from the opening of the first passage to the opening of the second passage in the surface of the substrate.

5. The sensing device according to claim 1, wherein the bypass passage has a maximum cross-sectional flow area that is larger than a maximum cross-sectional flow area of the continuous passage within the freestanding portion of the micromachined tube.

6. The sensing device according to claim 1, wherein the sealing material exclusively spaces apart the base of the micromachined tube and the surface of the substrate so as to exclusively define the gap therebetween.

7. The sensing device according to claim 6, wherein the sealing material contains particles, at least some of the particles contact both the base of the micromachined tube and the surface of the substrate so as to determine the gap therebetween.

8. The sensing device according to claim 1, further comprising a flow restrictor within the bypass passage.

9. The sensing device according to claim 1, further comprising means within the bypass passage for sensing a property of the fluid.

10. The sensing device according to claim 9, wherein the sensing means within the bypass passage senses a flow rate of the fluid through the bypass passage.

11. The sensing device according to claim 1, further comprising means for determining at least one of density, specific gravity, and chemical concentration of a fluid flowing through the continuous passage of the micromachined tube based on the resonant frequency of the freestanding portion of the micromachined tube.

12. The sensing device according to claim 11, further comprising a fuel mixture flowing through the continuous passage of the micromachined tube.

13. The sensing device according to claim 12, wherein the fuel mixture contains a fuel and the device measures the fuel concentration in the fuel mixture.

14. The sensing device according to claim 13, wherein the device is installed in a fuel cell system.

15. The sensing device according to claim 14, wherein the fuel cell system is installed in an electrical product chosen from the group consisting of computers, lap top computers, cellular telephones, digital cameras, video cameras, motorized vehicles, motorized bicycles, recharging stations, televisions, and radios.

16. The sensing device according to claim 1, further comprising means for sensing the temperature of the fluid flowing through the continuous passage of the micromachined tube.

17. The sensing device according to claim 1, further comprising means for determining a mass flow rate of the fluid flowing through the continuous passage of the micromachined tube based on the movement of the freestanding portion of the micromachined tube relative to the substrate.

18. The sensing device according to claim 1, further comprising;

means for determining at least one of density, specific gravity, and chemical concentration of a fluid flowing through the continuous passage of the micromachined tube based on the resonant frequency of the freestanding portion of the micromachined tube;

means for sensing the temperature of the fluid flowing through the device; and means for determining a mass flow rate of the fluid flowing through the device.

* * * * *